United States Patent [19]
Witte et al.

[11] Patent Number: 5,961,922
[45] Date of Patent: Oct. 5, 1999

[54] METHOD AND APPARATUS FOR DETECTING WATER ENTRAPMENT IN A VACCUM CHAMBER

[75] Inventors: Marcia Witte, Rancho Santa Margarita; Sebastian Eulogio, Irvine, both of Calif.

[73] Assignee: Johnson & Johnson Medical, Inc., Arlington, Tex.

[21] Appl. No.: 08/942,154

[22] Filed: Oct. 1, 1997

Related U.S. Application Data

[60] Provisional application No. 60/026,766, Oct. 4, 1996.

[51] Int. Cl.⁶ .................................................. A01N 9/00
[52] U.S. Cl. ............................... 422/33; 422/3; 422/292; 73/29.01; 73/29.03
[58] Field of Search ............................... 73/29.01, 29.03, 73/64.45, 64.46; 422/33, 3, 295, 112, 292; 436/38, 39, 148

[56] References Cited

U.S. PATENT DOCUMENTS

| | | | |
|---|---|---|---|
| 4,551,311 | 11/1985 | Lorenz | 422/300 |
| 4,643,876 | 2/1987 | Jacobs et al. | |
| 4,756,882 | 7/1988 | Jacobs et al. | |
| 5,317,896 | 6/1994 | Sheth et al. | |
| 5,482,683 | 1/1996 | Sheth et al. | |

*Primary Examiner*—Robert Warden
*Assistant Examiner*—Kaj K. Olsen
*Attorney, Agent, or Firm*—Andrew C. Farmer

[57] ABSTRACT

During a vacuum evacuation of a chamber, the presence of water in the chamber can be detected by monitoring the pressure level in the chamber. In the absence of water, the pressure will decrease continuously and smoothly. If water is present, the pressure will rise slightly one or more times, especially as the pressure falls below 5 torr. This rise in pressure can be detected to signal the unwanted presence of water in the chamber. The method has particular application to ensuring the chamber is free of water during the evacuation of a chamber employed in vapor or vapor/plasma sterilization.

16 Claims, 5 Drawing Sheets

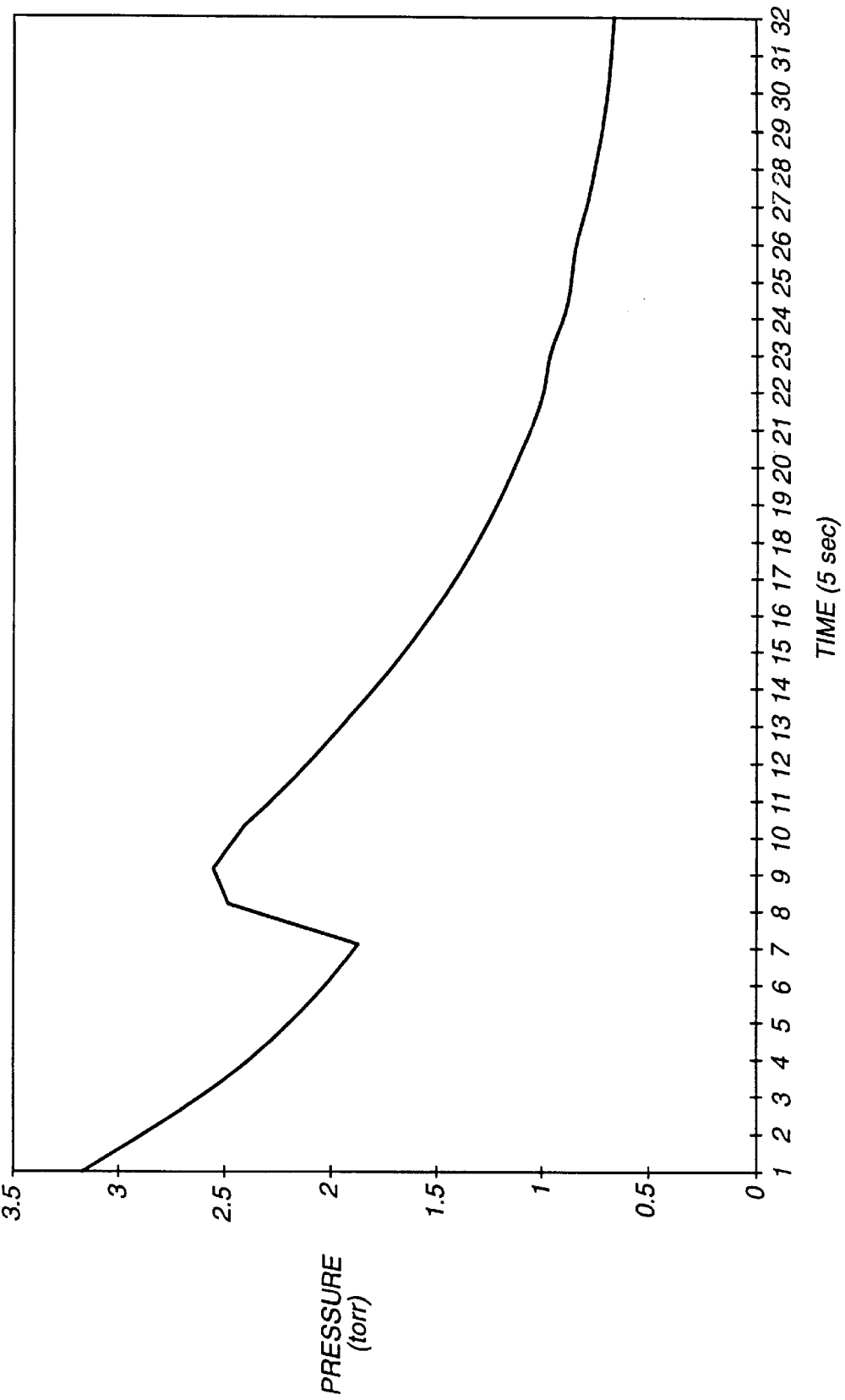

Background

METHOD AND APPARATUS FOR DETECTING WATER ENTRAPMENT IN A VACCUM CHAMBER

This application claims priority to U.S. Provisional Application No. 60/026,766 filed Oct. 4, 1996.

BACKGROUND

1. Field of the Invention

The present invention pertains to the detection of water in a chamber in which a vacuum is being drawn. It is particularly useful in chemical vapor sterilization techniques.

2. Background

In many instances having water in a vacuum chamber during the application of a vacuum is undesirable. The problem is of particular concern in chemical vapor sterilization techniques in which a chamber is drawn below atmospheric pressure.

A typical chemical vapor sterilization cycle begins by cleaning and drying the instruments to be sterilized and placing them into a chamber. The chamber is heated and the atmosphere in the chamber is evacuated. After achieving a strong vacuum, the vapor phase sterilizing agent is introduced into the chamber, either directly as a vapor or as a mist which quickly vaporizes in the vacuum. The vapor bathes the instruments killing bacteria, viruses and spores on the surfaces of the instrument in contact with the vapor. Hydrogen peroxide, ethylene oxide, and chlorine dioxide, among others, are suitable sterilants. A particularly advantageous system employs hydrogen peroxide vapor in connection with a gas plasma. The following U.S. Patents, incorporated fully herein by reference, describe such processes in more detail: U.S. Pat. Nos. 4,643,876 issued Feb. 17, 1987 to Jacobs et al. and 4,756,882 issued Jan. 27, 1987 to Jacobs et al.

To ensure that the hydrogen peroxide vapor will penetrate into cracks, crevices and particularly long lumens and the like in the instruments undergoing sterilization, air and water vapor in the chamber are evacuated prior to releasing the hydrogen peroxide vapor into the chamber. After the chamber is evacuated, the chemical vapor enters the chamber. The added vapor in the chamber slightly raises its pressure and the chemical vapor rushes to equalize the pressure throughout the chamber thereby quickly entering lumens and the like.

Water in the chamber inhibits complete permeation of the chamber, especially tight spaces, and full contact of the instruments with the chemical vapor through several mechanisms. Water vaporizing within the chamber dilutes the chemical vapor. In addition, if the water molecules have a higher diffusivity than the chemical vapor they will more efficiently reach the tight spaces, thereby reducing the concentration of the chemical vapor therein. Thus, water in the system can reduce the overall sterilization efficiency. Water initially present in the system as vapor will be removed as the system is drawn into vacuum. However, water initially present as liquid may vaporize either during the application of vacuum or afterwards to form water vapor present in the system. Water must vaporize to be eliminated from these systems.

Liquid water initially present in the system may cause additional problems by freezing as the vacuum is drawn. As a vacuum is drawn on the chamber, liquid water therein begins to evaporate as the total pressure in the chamber is decreased to the vapor pressure in the liquid. The liquid to vapor phase change requires heat and thus the water gives up its heat to evaporation and cools. When the water has cooled sufficiently, it freezes. The resulting ice particles may locally inhibit contact of the chemical vapor with the instrument, or in more severe cases may block narrow passageways. In nearly all sterilization methods, including hydrogen peroxide and hydrogen peroxide/gas plasma, operators know to check for the presence of liquids following the procedure, and if any liquids are detected the load is dried and the procedure repeated. Accordingly, it has long been desired to have some method of detecting the presence of liquid in a load to be sterilized prior to actually performing the sterilization process.

SUMMARY OF THE INVENTION

The present invention overcomes these and other problems by detecting the presence of liquid water during the process of drawing a vacuum. The present inventors have discovered that if the pressure is closely monitored during this process, transitory, minor increases in pressure indicate the presence of liquid water in the load. Upon detection of such transitory pressure increase, corrective action is taken, such as sounding an alert, terminating the cycle, placing a message on an operator's station or perhaps automatically initiating a cycle tending to eliminate the water from the load.

Preferably, such a process is automated with the aid of a microprocessor controlled or other such automatic control system. To reduce false indications of water, a running average of the pressure is preferably tested. Pressure variations of 50 millitorr signal the presence of an unacceptable amount of water in the system. This may be detected by sampling the pressure at predetermined intervals and calculating the peak volume of pressure increase for each transitory pressure peak. If the accumulated pressure rise in any peak reaches 50 millitorr that indicates the presence of excess water in the system in droplets of sufficient size to affect sterilization. The level at which a pressure peak triggers an indication of excess water can be tailored to individual circumstances, with lower levels giving more chance of false readings but enhanced sensitivity. Generally, monitoring for pressure increases should begin after the pressure in the chamber has fallen below 5 torr, such that the droplets are near the freezing point (triple point) for water.

It has been contemplated that the pressure increase occurs as a particular quantity of water, and even a small droplet can be detected, reaches the freezing point. The heat of fusion (energy released by the transformation from a liquid to a solid state) (90 cal/gm) becomes available to vaporize a quantity of water thereby initiating a rapid release of water vapor from the liquid particle which is detected as the pressure increase. The remainder of the particle freezes. The effectiveness of the method in predicting the presence of water has been verified through testing as disclosed in the examples.

BRIEF DESCRIPTION OF THE DRAWINGS

FIG. 5 is a graph of pressure versus time in the pressure chamber of the system of FIG. 1, with water entrapped within the system at one location.

DETAILED DESCRIPTION

Preferably, a fluid flow restriction is placed between a potential location of water and a pressure monitor. Preferably, the fluid flow restriction comprises an antimicrobial enclosure comprising a filter means for allowing the passage of vapor and restricting the passage of microbes.

Figure 1:
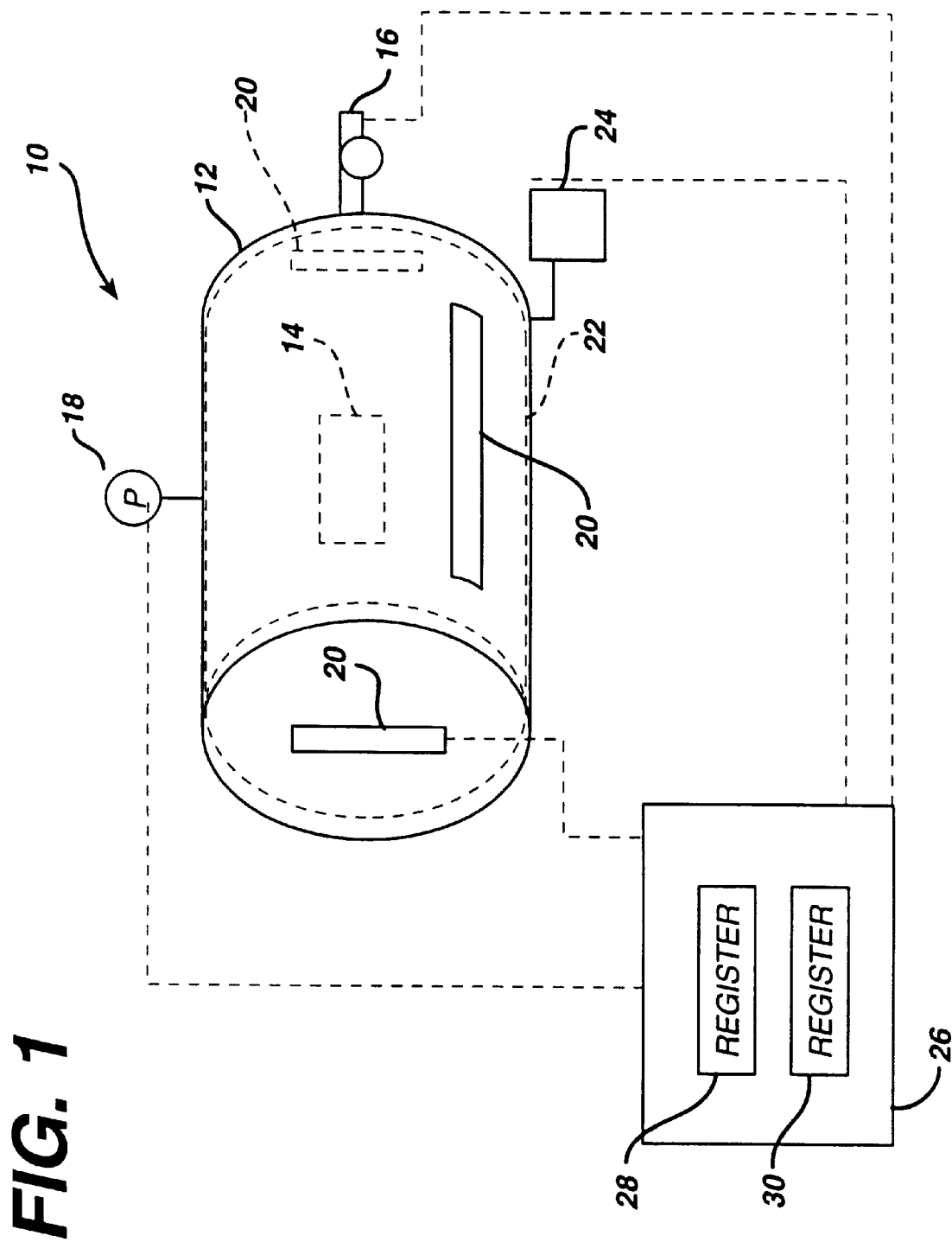
FIG. 1 depicts, in block diagram form, a sterilization system adapted to detect entrapped water according to the present invention.

Turning now to the drawings and to FIG. 1 in particular, a sterilization system 10 is depicted, generally in block diagram-format. It comprises in gross, a sterilization chamber 12 having a load 14 of instruments therein to be sterilized. The chamber 12 is formed of aluminum (any of several grades such as 6063 and 5052 are appropriate) stainless steel or glass. It normally operates at a vacuum as low as 3 torr and importantly does not interact with chemically, or absorb, hydrogen peroxide. A vacuum pump 16 capable of reaching the desired operating pressure evacuates air and other gases, such as vapor phase water, from the chamber 12. A pressure monitor 18 monitors the pressure in the system, preferably within±2.5 millitorr. Particularly suitable pressure monitors are capacitance manometers available from MKS Instruments or Varian Instruments. A heating element 20 heats the chamber 12. It preferably comprises separate elements bonded to the outside of the chamber 12 in locations sufficient to uniformly heat the chamber 12. An optional power source 24 and antenna 22 may be provided to excite a plasma within the chamber 12 during portions of the sterilization process.

A control system 26 controls the operation of the system 10 and its various components. The control system 26 may comprise any system presently known, or developed during the life of this patent, which one of skill in the art would recognize as being suitable for controlling the system 10. Preferably, the control system 26 will employ one or more microprocessors. In any event, it preferably will contain a pressure register 28, or the like, for monitoring the pressure in the chamber 12 and a pressure increase register 30, or the like, for monitoring the pressure increases in the chamber 12 during the time that the pump 16 is attempting to lower the pressure within the chamber 12.

In operation, the load 14 is cleaned of foreign matter, dried and placed into the chamber 12. Typically, it will be encased in a container with a filter, or wrapped in a filter material (neither of which are shown in FIG. 1) which will allow the passage of sterilizing vapor but will inhibit the passage of microbes to thereby preserve the sterility of the load 14 after sterilization is complete. During the process, the chamber is heated to between 42° and 50° C. After the chamber 12 is sealed, the control system 26 signals the pumping system 16 to evacuate the chamber 12. During the evacuation process, the pressure monitor 18 continuously monitors the pressure within the chamber 12. At a point during the evacuation where pressure increases would not normally be expected from a dry load 14, preferably below 5 torr, the control system 26 employs the method according to the present invention for detecting water entrapped in the chamber 12, and particularly in the load 14. Five torr is also just above the triple point pressure of water, 4.59 torr.

The control system 26 polls the pressure monitor 18 at predetermined intervals, as for instance every 100 milliseconds, and applies the value to the register 28 to monitor the running average pressure in the chamber 12. The running average may comprise the average of two or three pressure readings, but preferably comprises five or more. More preferably, the highest and lowest values are not included in the average. For instance, the running average may consist of the average of the previous five pressure readings, with the highest and lowest of the five being ignored.

If a new value of the running average pressure in register 28 exceeds the previous value, then the difference is added to the pressure increase register 30. The pressure increase register 30 has a minimum value of zero and is incremented or decremented by the difference between the latest and the previous value of the running average pressure register 28. If the value in register 30 exceeds 50 millitorr, it indicates the presence of water entrapped within the chamber 12. Upon the detection of entrapped water, the sterilization cycle is stopped, an the operator of the sterilization system 10 is informed to dry and repack the load 14. The indication of water in the load 14 may take several forms, such as a visual or audible alarm to the operator upon which the operator will know to physically redry and repack the load 14. Alternatively, the indication could trigger an automatic drying sequence within the chamber 12, such as by providing a dry atmosphere to the chamber 12, as for instance passing dry air through the chamber 12; or by applying energy to the chamber in a form likely to reach the water, as for example heating the atmosphere in the chamber or applying an electromagnetic field to the chamber 12 to excite the molecules in the water, as disclosed in copending U.S. application Ser. No. 08/320,392, (now U.S. Pat. No. 5,619,220) incorporated herein by reference.

Figure 2:
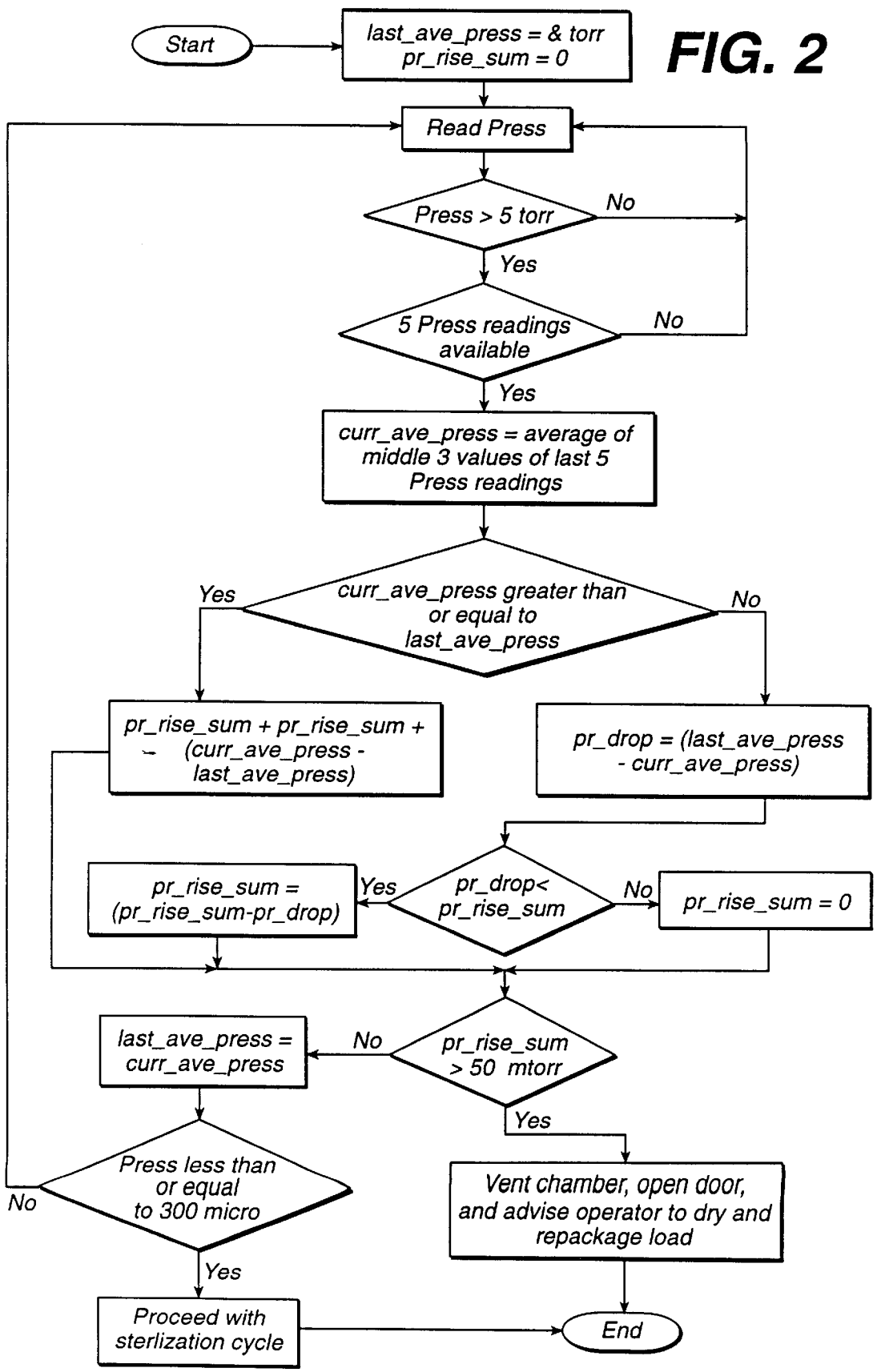
FIG. 2 is a flow diagram of a preferred embodiment of the method for detecting entrapped water according to the present invention.

The water entrapment test thus forms a portion of an overall operating protocol for the system 10. Preferably, the entire protocol, including the steps required to test for entrapped water, is embodied in software in the control system 26. Of course, hardwired logic or mechanical controls can be substituted for software controls. The flow chart of FIG. 2 illustrates the steps performed in carrying out the water entrapment test.

EXAMPLES

The method was tested under varying loading conditions to determine its effectiveness in locating water entrapped within the chamber 12. A STERRAD brand hydrogen peroxide/gas plasma sterilizer, available from Advanced Sterilization Products, a division of Johnson & Johnson Medical, Inc. and having offices in Irvine, Calif., was loaded with a simulated load of medical instruments for sterilization. Pump down (evacuation of the atmosphere) of the chamber 12 was initiated and the pressure was measured according to the method above to detect pressure increases of 5 millitorr during the last phase of the pump down, that is below 5 torr of chamber pressure.

If the water is outside of packing (on the surfaces of packaging) the method is not as sensitive as if the water is trapped within a device or package.

Total water content was varied, including values at 0.5 ml, 1.0 ml, 2.5 ml, 4.5 ml, and 6.0 ml. Several droplet sizes were used ranging from 0.25 ml to 3.0 ml. Three temperature levels were employed: Low (10° C.); room temperature (~22° C.); and High (40° C.). Two loading levels were tested: one of normal proportions to what can be expected in day-to-day sterilization in a hospital setting, and the other a heavy load including two flexible colonoscopes with polyurethane sheaths on their insertion portions. Outgassing loads, comprising a PVC tubing known to generate vapor from its surface in a vacuum, were employed in some of the runs. Objects containing PVC or other gas evolving substances are often found in normal hospital sterilization loads and their presence in these test loads ensures that the method does not falsely indicate the presence of water due to gases being released by the PVC in the vacuum. Two packaging levels were also tested: one in which trays containing the instruments are double wrapped with CSR (central supply room) wrap, a microbial barrier material which passes vapors, and the other in which instruments are packaged in two layers of a conventional pouch formed of TYVECK spun-bonded, non-woven, high-density polyethylene and MYLAR polyester film. Two different STERRAD 100 sterilizers were used to ensure that data was universal in vacuum systems. The test matrix is shown below in Table I and the results are shown in Table II.

TABLE I

TEST MATRIX

| Run No. | Water Level | Droplet Size | Temp of Load | Load Size | Outgassing Material | Packaging | Sterilizer |
|---|---|---|---|---|---|---|---|
| 1 | none | na | 10° C. | heavy | no | CSR Wraps/Pouches | I |
| 2 | none | na | 10° C. | 25 lbs SS rods + Normal Load | no | CSR Wraps | I |
| 3 | none | na | 40° C. | heavy | yes | CSR Wraps/Pouches | I |
| 4 | 2.5 ml | 1.25 ml drop in each tray | 10° C. | normal | no | CSR Wraps | I |
| 5 | 2.5 ml | 0.5 ml (one drop each in two pouches) | 40° C. | normal | no | CSR Wraps/Pouches | I |
| 6 | 4.5 ml | 2.25 ml drop in each tray | 40° C. | heavy | yes | CSR Wraps | I |
| 7 | 4.5 ml | 0.5 ml (two drops in each endoscope) | 10° C. | heavy | no | CSR Wraps/Pouches | II |
| 8 | 4.5 ml | 0.5 ml (two drops in each endoscope) | 10° C. | heavy | no | CSR Wraps/Pouches | II |
| 9 | 4.5 ml | 0.25 ml (one drop each in two pouches) | 40° C. | normal | no | CSR Wraps/Pouches | I |
| 10 | 4.5 ml | 0.25 ml (one drop each in two pouches) | 10° C. | heavy + 25 lbs SS rods | no | CSR Wraps/Pouches | I |
| 11 | 6.0 ml | 3.0 ml drop in each tray | 40° C. | heavy | yes | CSR Wraps | I |
| 12 | 6.0 ml | 0.25 ml (one drop each in two pouches) | 10° C. | heavy | no | CSR Wraps/Pouches | I |
| 13 | 6.0 ml | 0.5 ml (two drops in each endoscope) | 10° C. | heavy | no | CSR Wraps/Pouches | II |
| 14 | 6.0 ml | 0.25 ml (one drop each in two pouches) | 40° C. | normal | no | CSR Wraps/Pouches | I |
| 15 | 6.0 mol | 0.25 ml (one drop each in two pouches) | 10° C. | heavy + 25 lbs SS rods | no | CSR Wraps/Pouches | I |
| 16 | 1.0 ml | 0.25 ml (one drop each in two pouches) | 10° C. | heavy | no | CSR Wraps/Pouches | I |

TABLE I-continued

TEST MATRIX

| Run No. | Water Level | Droplet Size | Temp of Load | Load Size | Outgassing Material | Packaging | Sterilizer |
|---|---|---|---|---|---|---|---|
| 17 | 1.0 ml | 0.25 ml (one drop each in two pouches) | 40° C. | normal | no | CSR Wraps/ Pouches | I |
| 18 | 0.5 ml | 0.25 ml in vial per tray | room temp | heavy | No | CSR Wraps/ Pouches | I |
| 19 | 0.5 ml | 0.25 ml in vial per tray | 10° C. | heavy | no | CSR Wraps/ Pouches | I |

TABLE II

TEST RESULTS

| RUN # | PUMP DOWN | CYCLE | UPPER | LOWER | POUCHES | TOTAL CYCLE TIME |
|---|---|---|---|---|---|---|
| 1 | 14 min | Fail, low press. in injection | N/A | N/A | N/A | 30 mins |
| 2 | 6 min | Fail, low press. in injection | N/A | N/A | N/A | 22 mins |
| 3 | 15 min | Completed | N/A | N/A | N/A | 85 mins |
| 4 | 4 min | Fail, moisture in load | Water | Ice | N/A | 4 mins |
| 5 | 4 min | Fail, moisture in load | Ice | Water | Water | 4 mins |
| 6 | 4 min | Fail, moisture in load | Water | Ice | N/A | 4 mins |
| 7 | 4 min | Fail, moisture in load | Ice in vial & water in scopes | Ice in vial & water in scopes | N/A | 4 mins |
| 8 | 5 min | Fail, moisture in load | Water | Ice | Water | 5 mins |
| 9 | 3.5 min | Fail, moisture in load | Water | Ice | Water | 3 mins 30 sec |
| 10 | 4 min | Fail, moisture in load | Water | Ice | Water | 4 mins |
| 11 | 3.5 min | Fail, moisture in load | Water | Ice | N/A | 3 mins 30 sec |
| 12 | 5 min | Fail, moisture in load | Ice in vial & water in scopes | Water in scopes | N/A | 5 mins |
| 13 | 5 min | Fail, moisture in load | Ice | Ice | Water | 5 mins |
| 14 | 4 min | Fail, moisture in load | Ice | Ice | Water | 4 mins |
| 15 | 3 min | Fail, moisture in load | Water | Ice | Water | 3 mins |
| 16 | 4 min | Fail, moisture in load | Ice | Ice | Water | 4 mins |
| 17 | 3 min | Fail, moisture in load | Ice | Water | Ice | 3 mins |
| 18 | 16 min | Fail, low press. in injection | None | None | N/A | 32 mins |
| 19 | 15 min | Fail, low press. in injection | None | None | N/A | 31 mins |

The method accurately detected the water at all levels except at a total water load of 0.5 ml. The first two cycles without water failed merely due to the improper temperature at the start of the cycle. Once the chamber has been evacuated to a pressure of 300 millitorr, a cell in a hydrogen peroxide cassette is punctured and the contents (a measured quantity of highly concentrated hydrogen peroxide solution) are dropped into a heated metal cup in the chamber. Six minutes after the hydrogen peroxide is introduced into the chamber, if the pressure has not risen to 6 torr, the cycle is canceled for a "low pressure in injection." Failure of the pressure to increase indicates that not all of the hydrogen peroxide is in the vapor phase. These runs do indicate, however, that the method is not prone to making false positive indications. No load test was performed at 40° C. for 5 ml water since the increased latent heat in the load helps to vaporize that small amount.

Figure 3:
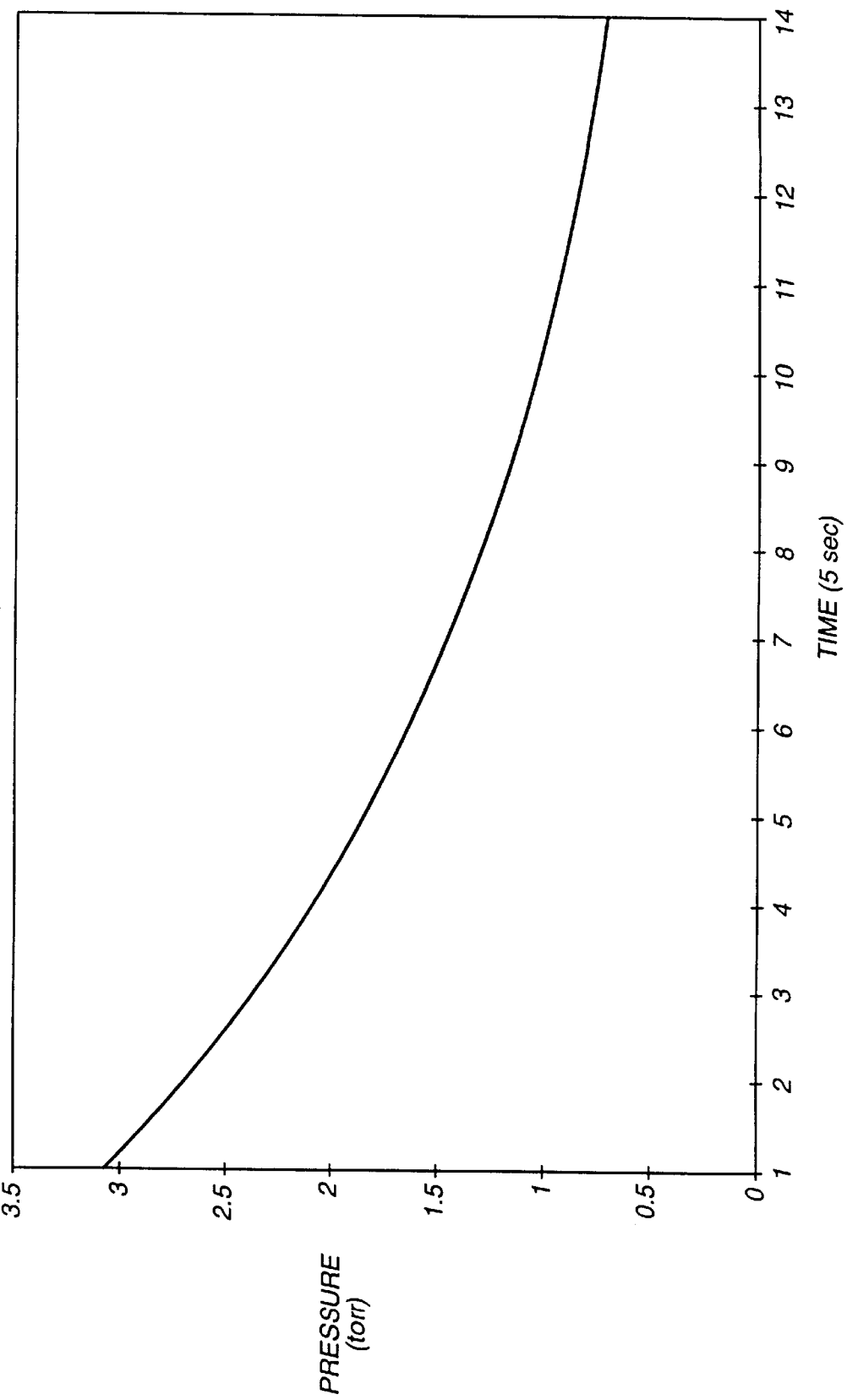
FIG. 3 is a graph of pressure versus time in a pressure chamber of the system of FIG. 1, without water entrapped within the chamber.
Figure 4:
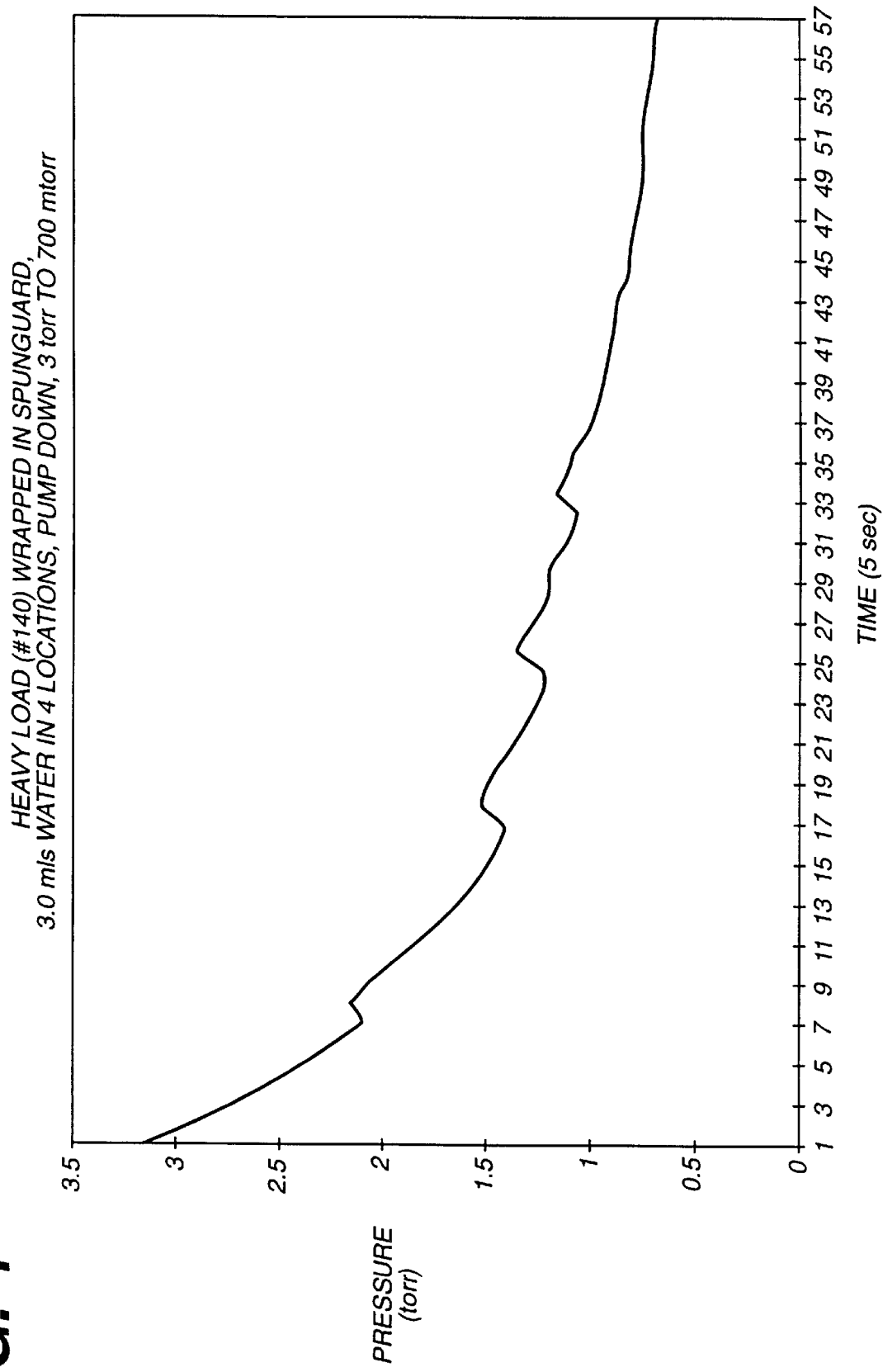
FIG. 4 is a graph of pressure versus time in the pressure chamber of the system of FIG. 1, with water entrapped within the system at four locations.

FIG. 3 illustrates the time versus pressure curve of that portion of the draw down where moisture is normally detected. Notice the smoothness of the curve. In this run, no water was present. FIG. 4 illustrates a similar portion of the cycle, but in this run 3.0 ml of water total was divided among four locations in the system. Notice the four separate pressure disturbances in the curve, corresponding to the four separate water locations. FIG. 5 illustrates a run in which 3.0 ml of water was placed in a single location. In this case, one large pressure variation is detected.

While the invention has been particularly described in connection with specific embodiments thereof, it is to be understood that this is by way of illustration and not of limitation, and that the scope of the appended claims should be construed as broadly as the prior art will permit.

What is claimed is:

1. A method for detecting the presence of water in a chamber while inducing a vacuum therein, the method comprising the steps of:

withdrawing the atmosphere from the chamber;

while the atmosphere is being withdrawn from the chamber, measuring the pressure level in the chamber and if the pressure level is below 5 torr and increases, indicating the presence of water in the chamber.

2. A method according to claim 1 wherein the step of indicating the presence of water is performed when the pressure in the chamber approaches the triple point pressure of water.

3. A method according to claim 1 wherein the step of indicating the presence of water is performed in response to a pressure increase exceeding a predetermined value.

4. A method according to claim 1 wherein the step of indicating the presence of water is performed after the pressure level increases by 50 millitorr or more.

5. A method according to claim 1 wherein the step of measuring the pressure level in the chamber comprises the steps of sampling the pressure at intervals and calculating a running average of the sampled pressure levels.

6. A method according to claim 5 wherein the step of indicating the presence of water is performed after the pressure level increases by 50 millitorr or more.

7. A method according to claim 1 wherein and further comprising the steps of sampling the pressure at predetermined intervals, calculating the cumulative increase in pressure for a transitory pressure peak, and if the cumulative increase in pressure for that transitory pressure peak reaches 50 millitorr, indicate the presence of excess water in the system.

8. A method for detecting the presence of water in a chamber while inducing a vacuum therein, the method comprising the steps of:

withdrawing the atmosphere from the chamber; placing a fluid flow restriction between a potential location of water and a pressure monitor;

while the atmosphere is being withdrawn from the chamber, measuring the pressure level in the chamber with the pressure monitor and if the pressure level is below 5 torr and increases, indicating the presence of water in the chamber.

9. A method according to claim 8 wherein the fluid flow restriction comprises an antimicrobial enclosure comprising a filter means for allowing the passage of vapor and restricting the passage of microbes.

10. A method for sterilizing an object comprising the steps of:

placing the object into a chamber having an atmosphere;

drawing at least a portion of the atmosphere out of the chamber;

measuring the pressure level in the chamber during the step of drawing the atmosphere out of the chamber and if the pressure level is below 5 torr and increases, then indicating the presence of water in the chamber and removing said water from the chamber;

injecting a sterilizing vapor into the chamber and contacting the object therewith.

11. A method according to claim 10 wherein the step of measuring the pressure level in the chamber comprises the steps of sampling the pressure at intervals and calculating a running average of the sampled pressure levels.

12. An apparatus for sterilizing an object, the apparatus comprising:

a chamber having an interior space capable of receiving the object a vacuum means for extracting at least a portion of an atmosphere from the interior space;

means for detecting a pressure within the chamber;

and an indicating means for indicating the presence of water in the chamber in response to an increase in pressure while the vacuum means is extracting atmosphere from the chamber.

13. An apparatus according to claim 12 wherein the is responsive only below a predetermined pressure.

14. An apparatus according to claim 13 wherein the predetermined pressure is 5 torr.

15. An apparatus according to claim 12 wherein the in pressure is responsive only to increases in pressure exceeding a predetermined value.

16. An apparatus according to claim 15 wherein the predetermined value is 50 millitorr.

* * * * *

UNITED STATES PATENT AND TRADEMARK OFFICE
CERTIFICATE OF CORRECTION

PATENT NO. : 5,961,922
DATED : October 5, 1999
INVENTOR(S) : Marcia Witte and Sebastian Eulogio It is certified that error appears in the above-identified patent and that said Letters Patent is hereby corrected as shown below:

Claim 13 - delete in its entirety and read as follows:

"An apparatus according to claim 12 wherein the indicating means is responsive only below a predetermined pressure."

Claim 15 - delete in its entirety and read as follows:

"An apparatus according to claim 12 wherein the indicating means is responsive only to increases in pressure exceeding a predetermined value."

Signed and Sealed this

Twenty-seventh Day of June, 2000

Q. TODD DICKINSON

*Attest:*

*Attesting Officer*          *Director of Patents and Trademarks*